United States Patent
Jeong et al.

(10) Patent No.: US 11,737,722 B2
(45) Date of Patent: Aug. 29, 2023

(54) X-RAY DETECTOR HAVING FABRICATION FAULT TOLERANT STRUCTURE AND FABRICATION METHOD THEREOF

(71) Applicants: RAYENCE Co., Ltd., Gyeonggi-do (KR); VATECH EWOO Holdings Co., Ltd., Gyeonggi-do (KR); Qpix solutions Inc., Durham, NC (US)

(72) Inventors: Jin Woong Jeong, Gyeonggi-do (KR); Ho Seok Lee, Gyeonggi-do (KR); Chang Hyeuk Kim, Apex, NC (US); Seungman Yun, Durham, NC (US)

(73) Assignees: RAYENCE Co., Ltd., Gyeonggi-do (KR); VATECH EWOO Holdings Co., Ltd., Gyeonggi-do (KR); Qpix solutions Inc., Durham, NC (US)

( * ) Notice: Subject to any disclaimer, the term of this patent is extended or adjusted under 35 U.S.C. 154(b) by 0 days.

(21) Appl. No.: 17/837,838

(22) Filed: Jun. 10, 2022

(65) Prior Publication Data

US 2022/0395249 A1 Dec. 15, 2022

Related U.S. Application Data

(60) Provisional application No. 63/209,254, filed on Jun. 10, 2021.

(51) Int. Cl.
*A61B 6/00* (2006.01)
*G01T 1/16* (2006.01)
*B41F 16/00* (2006.01)

(52) U.S. Cl.
CPC ............... *A61B 6/584* (2013.01); *G01T 1/16* (2013.01); *B41F 16/00* (2013.01)

(58) Field of Classification Search
CPC ............ A61B 6/584; G01T 1/16; B41F 16/00
See application file for complete search history.

(56) References Cited

U.S. PATENT DOCUMENTS

| 5,886,353 A | * | 3/1999 | Spivey | ...................... H04N 5/32 |
| | | | | 250/580 |
| 6,075,248 A | * | 6/2000 | Jeromin | ............ H01L 27/14623 |
| | | | | 257/E27.141 |

(Continued)

FOREIGN PATENT DOCUMENTS

| JP | 3976915 B2 * | 9/2007 | ....... H01L 27/14676 |
| JP | 3978971 B2 * | 9/2007 | |

*Primary Examiner* — Hugh Maupin
(74) *Attorney, Agent, or Firm* — IP Legal Services, LLC

(57) ABSTRACT

Provided are an X-ray detector having fabrication fault tolerant structure and a method for manufacturing the same using a micro-transfer printing (MTP) technique. The X-ray detector may include a photodiode layer formed on a base substrate within a pixel area and including a plurality of photodiode pixel units, a dummy layer formed the base substrate within a peripheral area, a plurality of pixel driving integrated chips printed on the photodiode layer, a plurality of primary column and row integrated chips printed on the dummy layer, and metal lines coupling the column and row integrated chips with pixel driving integrated chips and other constituent elements, wherein the plurality of pixel driving integrated chips and primary column and row integrated chips are manufactured separately from the photodiode layer and the dummy layer and attached on the photodiode layer and the dummy layer, respectively.

20 Claims, 13 Drawing Sheets

(56) References Cited

U.S. PATENT DOCUMENTS

| | | | |
|---|---|---|---|
| 6,242,746 B1 * | 6/2001 | Teranuma | H01L 27/14676 257/E27.111 |
| 2013/0334431 A1 * | 12/2013 | Ichimura | H01L 27/1462 257/59 |
| 2014/0334601 A1 * | 11/2014 | Shizukuishi | A61B 5/0062 378/62 |
| 2015/0034944 A1 * | 2/2015 | Cho | H01L 27/1288 257/53 |
| 2020/0379132 A1 * | 12/2020 | Na | G01T 1/2018 |

* cited by examiner (A)          (B)

X-RAY DETECTOR HAVING FABRICATION FAULT TOLERANT STRUCTURE AND FABRICATION METHOD THEREOF

CROSS REFERENCE TO PRIOR APPLICATIONS

This application claims the benefit of the filing date of U.S. Patent Provisional Application Ser. No. 63/209,254, filed Jun. 10, 2021, the teaches of which are incorporated herein their entirety by reference.

The submit matter of this application is related to U.S. patent application Ser. No. 16/731,007, filed Dec. 30, 2019, the teaches of which are incorporated herein their entirety by reference.

BACKGROUND

The present disclosure relates to an X-ray detector having fabrication fault tolerant structure and a method for manufacturing the same using a micro-transfer printing (MTP) technique.

In medical or industrial radiography, a digital X-ray detector has been widely used. Such a digital X-ray detector may be commonly referred to as an X-ray detector, an image detector, or an X-ray image sensor. Further, such a digital detector may be classified into an indirect conversion type X-ray detector and a direct conversion type X-ray detector. The indirect conversion type X-ray detector i) converts X-rays (e.g., X-ray photons) into visible light (e.g., light photons) using a scintillator and ii) converts the visible light into an electric signal. The direct conversion digital detector directly converts X-rays into an electric signal using a photoconductive layer.

As described, an X-ray detector detects X-ray signals that are radiated from an X-ray source, have passed through a target object, and reached to the X-ray detector. The X-ray detector converts the detected X-ray signals into electric signals. Such an X-ray detector includes a pixel array panel including a plurality of pixels. Each pixel includes a light receiving element (e.g., photoconductor or photodiode) and a driving element for driving the light receiving element of each pixel.

Such an X-ray detector (e.g., photodiode) may be manufactured using a thin-film transistor (TFT) process or a complementary metal-oxide-semiconductor (CMOS) process. The TFT process is advantageous for manufacturing a large surface X-ray detector with a low manufacture unit price. The CMOS process is advantageous for manufacturing a high image quality X-ray detector generating comparably low radiation dose and having a dynamic imaging capability. However, the TFT process may have limitations for manufacturing a high image quality X-ray detector because it is difficult to form metal lines in a nanometer level due to a high temperature chamber and an amorphous process. The CMOS process may have limitations for manufacturing a large surface X-ray detector because of a silicon wafer size.

In order to overcome shortcomings of the TFT process and the CMOS process, Micro-Transfer Printing (MTP) has been introduced. Such micro-transfer printing is a process of fabricating a semiconductor by picking up functional microstructures made in dense arrays on a source substrate, such as silicon wafer, and transferring the picked-up microstructures on a destination substrate using a viscoelastic stamp. Such micro-transfer printing is a method for manufacturing an X-ray detector while maintaining advantages of both the TFT process and the CMOS process. Further, the micro-transfer printing enables mass production with a low manufacturing cost.

In generally, an X-ray detector includes i) pixel integrated chips (ICs) formed in a pixel area and ii) column and row integrated chips (ICs) formed in a peripheral area. The column and row integrated chips (ICs) are formed or printed directly on a base substrate in the peripheral area. Unlike the column and row ICs, the pixel ICs are formed or printed on photodiodes (e.g., photodiode layer) which is formed on the base substrate. Accordingly, there is a height difference between the column and row ICs and the pixel ICs because of the photodiodes only formed in the pixel area. After printing or forming the column and row ICs and the pixel ICs, the column and row ICs are coupled to corresponding pixel ICs by printing or forming metal lines. In the printing or forming the metal lines, the height difference degrades printing efficiency and causes line defect. As a result, an entire X-ray detector could be discarded because of the height difference.

SUMMARY

In accordance with an aspect of the present embodiment, an X-ray detector may include a structure for minimizing line defects in printing or forming lines coupling pixel ICs and column and row ICs and for improving fabrication fault tolerant In accordance with another aspect of the present embodiment, an X-ray detector may include a dummy layer formed on a base structure within a peripheral area.

In accordance with still another aspect of the present embodiment, an X-ray detector may include secondary column and row integrated chips printed respectively with primary column and row integrated chips for improving fabrication fault tolerance.

In accordance with further another aspect of the present embodiment, a method for fabricating an X-ray detector may include forming a dummy layer on a base structure within a peripheral area.

In accordance with yet another aspect of the present embodiment, a method for fabricating an X-ray detector may include printing secondary column and row ICs within a peripheral area.

In accordance with further still another aspect of the present embodiment, a method for fabricating an X-ray detector may include inspecting each column and row IC and replacing the inspected column and row IC with a corresponding secondary column and row IC when the inspected column and row IC is determined as malfunctioned.

In accordance with yet another embodiment, an X-ray detector may include a photodiode layer formed on a base substrate within a pixel area and including a plurality of photodiode pixel units, a dummy layer formed the base substrate within a peripheral area, a plurality of pixel driving integrated chips printed on the photodiode layer, a plurality of primary column and row integrated chips printed on the dummy layer, and metal lines coupling the column and row integrated chips with pixel driving integrated chips and other constituent elements, wherein the plurality of pixel driving integrated chips and primary column and row integrated chips are manufactured separately from the photodiode layer and the dummy layer and attached on the photodiode layer and the dummy layer, respectively.

In accordance with another embodiment, a method for manufacturing an X-ray detector may include forming a photodiode layer on a base substrate within a pixel area, wherein the photodiode layer includes a plurality of photodiodes and configured to receive X-ray that have passed through a target object and convert the received X-ray to electric signals, forming a dummy layer on the base substrate within a peripheral area, printing a plurality of pixel driving integrated chips on the photodiode layer, printing a plurality of primary column and row integrated chips on the dummy layer, and printing metal lines coupling the column and row integrated chips with pixel driving integrated chips and other constituent elements, wherein the plurality of pixel driving integrated chips and primary column and row integrated chips are manufactured separately from the photodiode layer and the dummy layer and attached on the photodiode layer and the dummy layer, respectively.

DETAILED DESCRIPTION OF EMBODIMENTS

Figure 1:
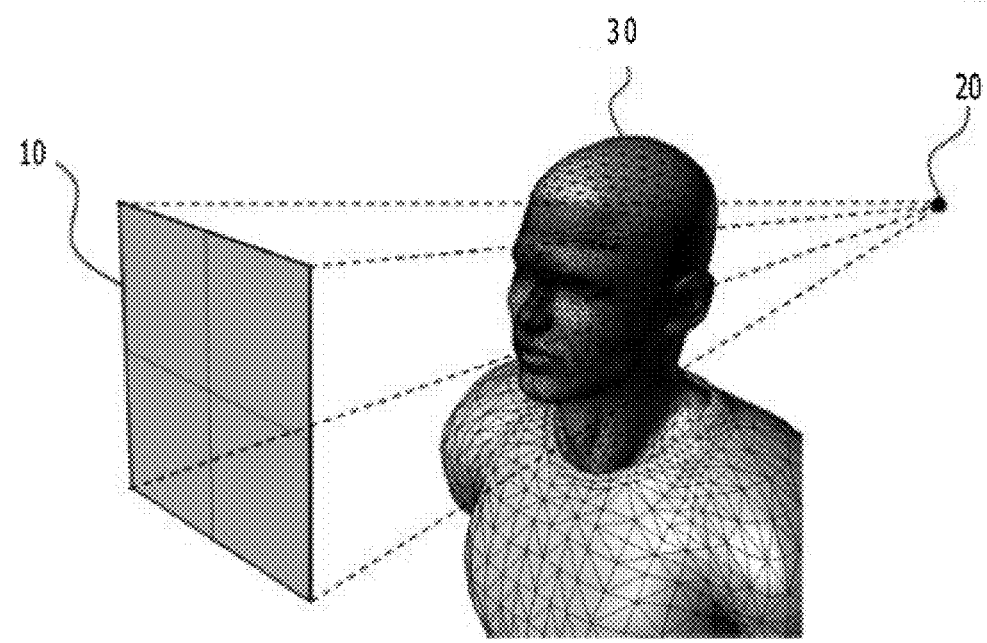
FIG. 1 is a view illustrating an X-ray detector receiving X-ray transmitted form an X-ray source and passed through a target object in accordance with at least one embodiment.

In accordance with at least one embodiment, an X-ray detector may have a comparatively simple structure that allows to be manufactured in a mass production method. The X-ray detector according to at least one embodiment may have a fabrication fault tolerant structure that minimizes line defects (e.g., line printing or forming defects) in a micro-transfer printing (MTP) process and that improves fabrication fault tolerance. In particular, the X-ray detector may include i) a photodiode layer formed within a pixel area, ii) a dummy layer formed within a peripheral area at the same level of the photodiode layer, iii) column and row micro integrated chips (ICs) printed on the dummy layer, and iv) a plurality of pixel driving micro integrated chips (ICs) printed on the photodiode layer, where the column and row ICs and the pixel driving micro ICs are fabricated separately from the dummy layer and the photodiode layer and respectively printed on a top of the dummy layer and the photodiode layer, through a micro-transfer printing technology. Further, the X-ray detector may include a secondary column and row micro integrated chips (ICs) formed on the peripheral area, where the secondary column and row micro integrated chips (ICs) may be activated when a primary column and row micro integrated chips (ICs) are determined as malfunctioning.

The dummy layer and the photodiode layer may be fabricated using a thin-film transistor (TFT) process which is advantageous in manufacturing a large surface detector at a low unit manufacturing price, and the column and row micro integrated chips and the pixel driving micro integrated chips may be fabricated using a complementary metal-oxide-semiconductor (CMOS) process which is advantages in manufacturing a detector with high precision and high quality.

In accordance with at least one embodiment, the column and row micro integrated chips and the pixel driving micro integrated chips may be formed on a source silicon wafer, transferred on an elastomer stamp, and respectively printed on the dummy layer and the photodiode layer using the elastomer stamp.

Accordingly, the X-ray detector according to an embodiment may have a structure to be manufactured through a mass production method while maintaining the high image quality. Furthermore, the X-ray detector according to an embodiment may have a structure (e.g., the column and row ICs formed on the dummy layer) that significantly reduces or even eliminates the height difference of the pixel driving IC and the column and row ICs. In addition, X-ray detector according to an embodiment may have redundant column and row ICs (e.g., secondary column and row ICs) for improving fabrication fault tolerance.

Hereinafter, the X-ray detector and the method for manufacturing the same according to embodiments will be described with reference to the accompanying drawings. For convenience of describing and ease of understanding, an X-ray detector may representatively denote a detector receiving X-ray (e.g., X-ray photons) passed through a target object and generating electric signals by converting the received X-ray photons. However, the embodiments of the present disclosure are not limited thereto. The X-ray detector may be referred as an imaging detector, an image sensor, a digital detector, and so forth.

FIG. 1 is a view illustrating an X-ray detector receiving X-ray (e.g., X-ray photons) transmitted form an X-ray source and passed through a target object in accordance with at least one embodiment.

Referring to FIG. 1, X-ray detector 10 and X-ray source 20 may be respectively installed and disposed to face each other. X-ray source 20 may generate X-ray (e.g., X-ray photons) and radiate the generated X-ray toward target object 30, such as a patient.

X-ray detector 10 may i) receive X-ray (e.g., X-ray photons) that are generated from X-ray source 20 and passed through target object 30 and ii) convert the received X-ray (e.g., X-ray photons) indirectly or directly to electric signals in accordance with at least one embodiment. X-ray detector 20 may have a rectangular shape in plan, but the shape of X-ray detector 20 is not limited to thereto.

In accordance with at least one embodiment, X-ray detector 10 may be an indirect type X-ray detector that receives X-ray (e.g., X-ray photons) passed through target object 30, converts the X-ray (e.g., X-ray photons) to visible light photons, and converts the visible light photons into the electric signals. Accordingly, X-ray detector 10 may include a scintillator layer for converting X-rays photons into visible light photons. Such a scintillator layer may be made of cesium iodide (CsI), but the embodiments of the present disclosure are not limited thereto. For example, X-ray detector 10 may be a direct type X-ray detector that converts the X-ray (e.g., X-ray photons) directly to electrical signals. In case of the direct type X-ray detector, X-ray detector 10 may exclude the scintillator layer. Further, the direct type X-ray detector may include a photoconductor layer.

In accordance with at least one embodiment, X-ray detector 10 may include a plurality of pixel driving micro integrated chips (ICs) and column and row micro integrated chips (ICs) that are separately fabricated from a photodiode layer and a dummy layer by using a manufacturing method allowing high precision fabrication different from that for manufacturing a photodiode layer and a dummy layer and are printed on a top of the photodiode layer and the dummy layer, using a micro-transfer printing technology.

In accordance with another embodiment, X-ray detector 10 may further include secondary column and row micro integrated chips, which may be activated when a primary column and row micro integrated chips are malfunctioning.

Figure 2:
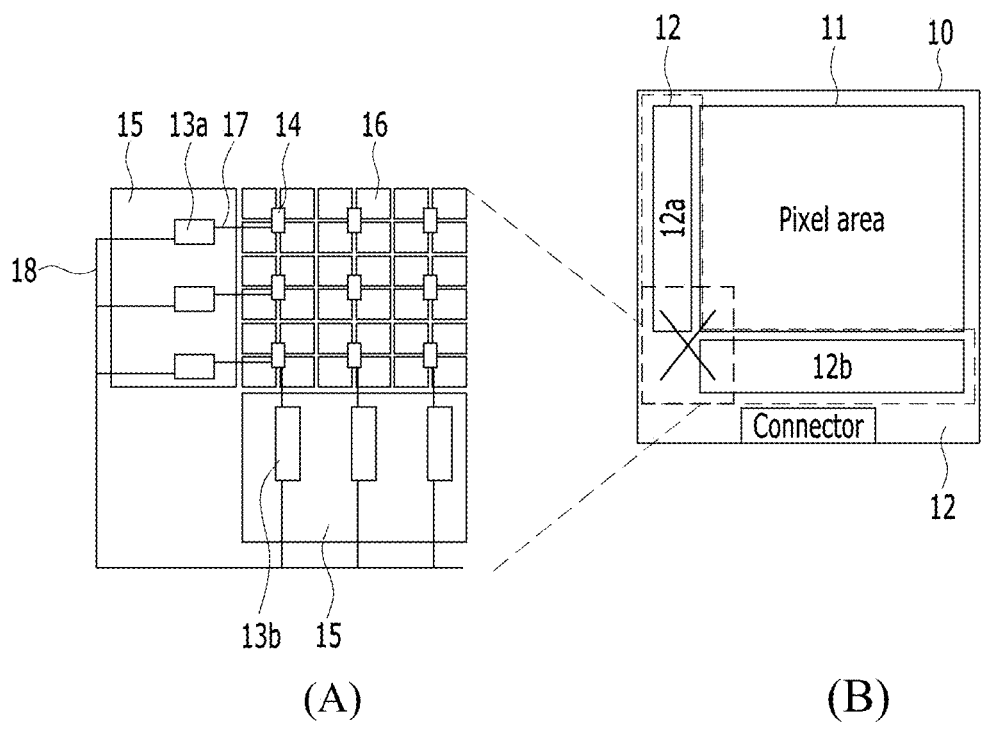
FIG. 2 illustrates an internal structure of an X-ray detector in accordance with at least one embodiment.

Hereinafter, such a fault tolerant structure of X-ray detector 10 will be described in more detail with reference to FIG. 2. FIG. 2 illustrates an internal structure of an X-ray detector in accordance with at least one embodiment. In FIG. 2, a diagram (B) illustrates pixel area 11 and peripheral area 12 of X-ray detector 10, and a diagram (A) is a magnified view of a part X in the diagram (B).

Referring to FIG. 2, X-ray detector 10 may include pixel area 11 and peripheral area 12 as shown in the diagram (B). Further, peripheral area 12 may include row integrated chip (IC) area 12a and a column integrated chip (IC) area 12b. Row ICs 13a may be printed on row IC area 12a. Row ICs 13a may be referred to as a gate driver circuit. Column ICs 13b may be printed on column IC area 12b, and column ICs 13b may be referred to as data driver circuit 13b.

Pixel area 11 may be referred to as pixel circuit area 11 and include a plurality of pixels, also referred to as photodiode pixel units. Pixel area 11 may be a main panel that receives X-ray photons, converts X-ray (e.g., X-ray photons) to visible light photons, and converts light photons to electric signals. That is, pixel area circuit 11 may be an indirect conversion type in accordance with at least one embodiment. However, the embodiments of the present disclosure are not limited thereto. For example, pixel area circuit 11 in another embodiment may be a direct conversion type. In the direct conversion type, pixel area circuit 11 excludes a scintillator layer and converts X-ray (e.g., X-ray photons) directly to electric signals using a photoconductor layer.

As shown in FIG. 2, pixel area 11 may include a plurality of pixels P, each serving as a unit photo-electric conversion element, arranged in matrix in accordance with at least one embodiment. Each pixel P may be a unit of a light receiving element (e.g., light conversion element). Each pixel P may include a photodiode that converts the incident light into the electrical signals. A pixel micro integrated chip (IC) may be connected to a plurality of the photodiodes.

Typically, each pixel P includes a pixel driving element for controlling a corresponding pixel to read a signal accumulated therein. Each pixel P may be referred to as photodiode pixel unit. Unlike the typical art, pixel P does not include a pixel driving element in accordance with at least one embodiment. In accordance with at least one embodiment, pixel area 11 may include a plurality of pixel driving micro integrated chips (ICs) 14 that are separated fabricated from a photodiode layer and printed on the photodiode layer using a micro-transfer printing technology. The micro-transfer printing technology may use an elastomer stamp to print devices (e.g., pixel driving micro integrated chips) on a target panel (e.g., a photodiode layer).

In particular, the plurality of micro driving integrated chips may be fabricated on a source silicon wafer, for example, using a CMOS process, the plurality of fabricated micro driving integrated chips may be transferred onto an elastomer stamp, and the plurality of fabricated micro driving integrated chips may be printed on the photodiode layer by stamping the elastomer stamp on the photodiode layer.

In accordance with one embodiment, peripheral area 12 may include row integrated chip (IC) area 12a and column integrated chip (IC) area 12b. Each pixel P may be coupled to row IC 13a (e.g., gate driver circuit) and column IC 13b (e.g., data driver circuit) formed in peripheral area 12. In particular, each pixel P may be coupled to row IC 13a (e.g., gate driver circuit) through gate lines 17a formed to extend in a row direction and to column IC 13b (e.g., data driver circuit) through data lines 17b formed to extend in a column direction.

Row IC 13a (e.g., gate driver circuit) may control the timing of output of a gate signal according to the gate control signal supplied from a control circuit (now shown). Column IC 13b (e.g., data driver circuit) read outs the data accumulated in the pixels P. The read out data D may be delivered to the control circuit. Column IC 13b may be controlled based on the data control signal supplied from the control circuit.

Referring to FIG. 2 again, X-ray detector 10 may include column and row micro integrated chips (ICs) area 12, and row ICs 13a and column ICs 13b are printed on dummy layer 15 formed in column and row micro ICs area 12 in accordance with at least one embodiment. In particular, dummy layer 15 may be formed on a base substrate in order to compensate a height difference between the photodiode layer and the base substrate.

In accordance with at least one embodiment, column and row micro integrated chips 12a and 12b may be separately fabricated from a dummy layer formed on a base layer and printed on the dummy layer using a micro-transfer printing technology. The micro-transfer printing technology may use an elastomer stamp to print devices (e.g., column and row micro integrated chips on a target panel (e.g., a dummy layer) as described above. In particular, the plurality of column and row micro integrated chips may be fabricated on a source silicon wafer, for example, using a CMOS process, the plurality of fabricated micro integrated chips may be transferred onto an elastomer stamp, and the plurality of fabricated micro integrated chips may be printed on the dummy layer by stamping the elastomer stamp on the photodiode layer.

As described, dummy layer may be formed to compensate the height difference between the photodiode layer and the base substrate at the peripheral area in accordance with at least one embodiment. Such dummy layer may significantly reduce or eliminate line defect when the line is printed to respectively couple the column and row ICs to the pixel ICs. The line defect, the height difference, and the dummy layer will be described in more detail with reference to FIG. 3A, FIG. 3B, FIG. 4A and FIG. 4B, hereinafter.

Figure 3A:
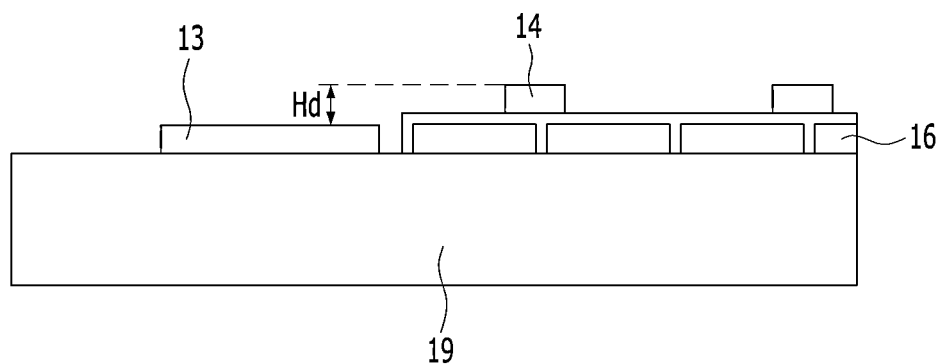
FIG. 3A is a cross-sectional view of an X-ray detector for explaining height difference between a column and row IC and a pixel IC.

FIG. 3A is a cross-sectional view of an X-ray detector for explaining a height difference between a column and row IC and a pixel IC. Referring to FIG. 3A, photodiode array 16 is formed on a Glass Panel (e.g., base substrate) used as a TFT panel within a pixel area. Such a photodiode array is patterned into photodiode pixel units, and pixel IC 14 is printed on the photodiode pixel units for driving corresponding photodiode pixel units.

In addition, column and row ICs 13 (e.g., peripheral IC) are formed directly on a base substrate, such as the glass panel, within a peripheral area. Since column and row ICs 13 is formed directly on the base substrate, a height of column and row ICs 13 is lower to that of pixel ICs 14. That is, there is height difference Hd between the column and row ICs 13 and pixel ICs 14, as shown in FIG. 3A.

Figure 3B:
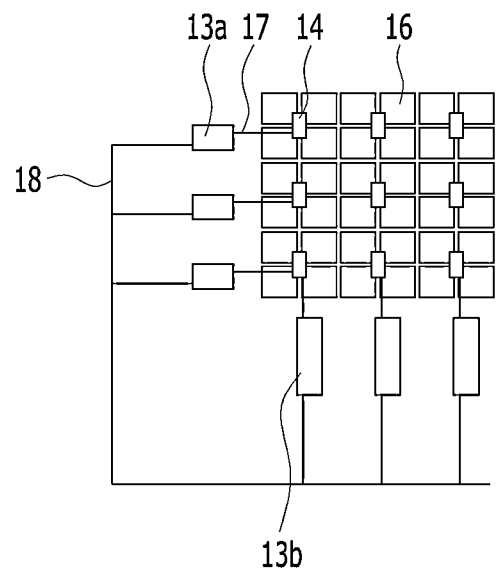
FIG. 3B is a top view of an X-ray detector for explaining line defects caused in a line printing process.

FIG. 3B is a top view of a typical X-ray detector for explaining line defects caused in a line printing process. Referring to FIG. 3B, the line printing process is performed after forming column and row ICs 13 directly on a base substrate and forming pixel ICs 14 on photodiode 16. That is, data lines 17a and 17b are formed to couple column and row ICs 13 formed direction on base substrate and pixel IC 14 formed on photodiode layer 16. Further, column and row ICs 13a and 13b are coupled to a power supply (not shown) through power lines 18 by the line printing process.

Due to the height difference Hd, line defects may be caused during the line printing process. That is, such a typical fabricating method may cause line defects due to the height difference Hd.

Figure 4A:
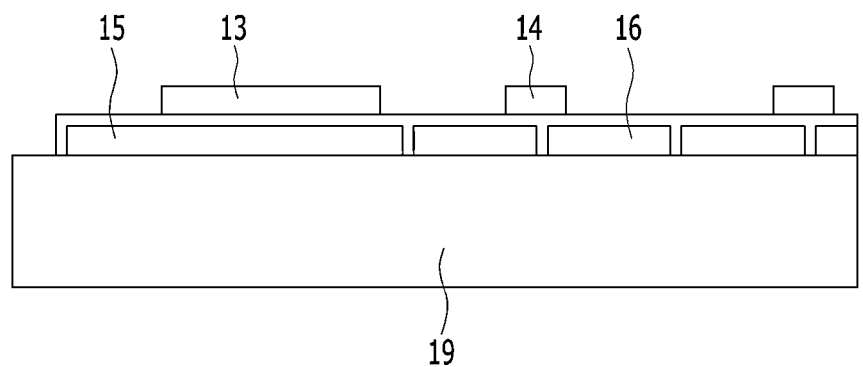
FIG. 4A is a cross-sectional view of an X-ray detector including a dummy layer in accordance with at least one embodiment.

To overcome such a shortcoming, a dummy layer is formed on a base substrate within a peripheral area in accordance with at least one embodiment. Hereinafter, the dummy layer will be described in more detail with reference to FIG. 4A and FIG. 4B. FIG. 4A is a cross-sectional view of an X-ray detector including a dummy layer in accordance with at least one embodiment.

Referring to FIG. 4A, dummy layer 15 may be formed in the peripheral area to compensate the height difference Hd between column and row ICs 13 and pixel ICs 14 in accordance with one embodiment. Dummy layer 15 may be formed to have height similar or equal to that of photodiode layer 16. Accordingly, forming dummy layer may minimize line defect in the post line printing process.

In accordance with at least one embodiment, dummy layer 15 may be formed with various material. For example, dielectric material such as $SiO_2$ or $SiN_x$ may be used for forming dummy layer 15. Further, epoxy resin may be used for forming dummy layer 15.

In accordance with at least one embodiment, dummy layer 15 may be formed to have height (e.g., thickness) similar or equal to that of photodiode layer 16. However, the embodiments are not limited thereto. The height (e.g., thickness) of dummy layer 15 may be determined based on predetermined factors including types of material used for forming an interlayer dielectric layer and an adhesive layer and a tolerable range of lines to be printed to couple column and row ICs and pixel ICs. For example, the tolerable range of lines for line printing may be about 3 um.

In accordance with at least one embodiment, various methods may be used for forming dummy layer 15. Such a fabrication method of forming dummy layer 15 may be determined based on predetermined factors including a type of material used for forming photodiode layer 16 and dummy layer 15. For example, in case of a-Si photodiode, a large surface deposition method such as plasma enhanced chemical vapor deposition (PECVD) or chemical vapor deposition (CVD) may be used. In case of using interlayer dielectric material such as $SiO_2$ or $SiN_x$, a large surface deposition method PECVD, CVD, or physical vapor deposition (PVD) may be used.

Further, in case of using polymer/epoxy resin, dummy layer 15 may be formed by applying (or depositing) polymer or epoxy resin through spray-coating or slot-die coating and hardening the deposited polymer or epoxy resin by using ultra violet ray, thermohardening, or natural hardening.

Figure 8:
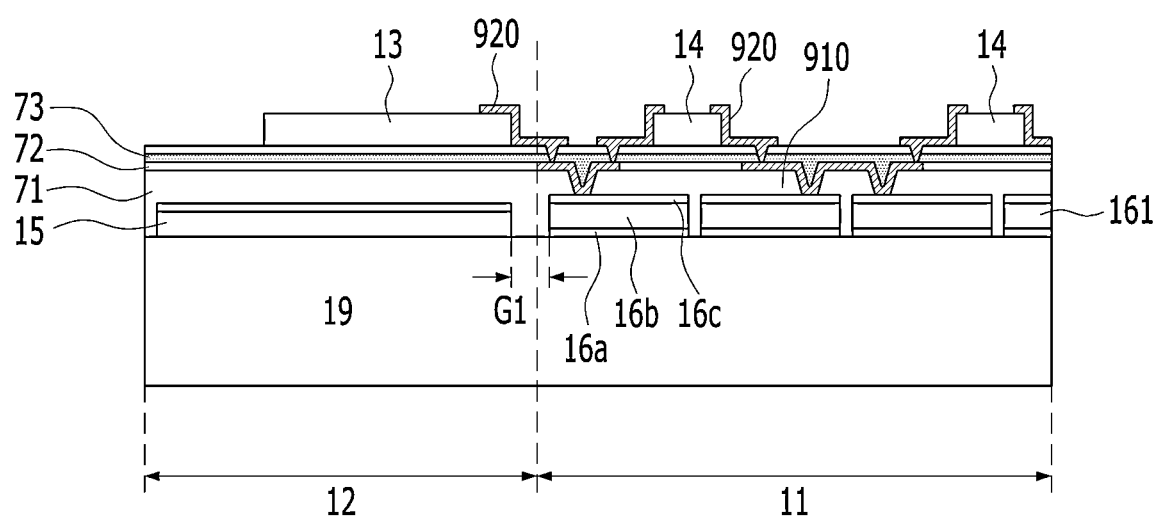
FIG. 8 is a cross-sectional view of a predetermined section in a peripheral area and a pixel area of an X-ray detector in accordance with one embodiment.

In accordance with another embodiment, dummy layer 15 may be formed by continuously forming photodiode layer 16 on base substrate 19 in peripheral area 12 and patterning photodiode layer 16 in pheripheral area 12 to dummy photodiode layer 15' and to have a gap (G) between dummy photodiode layer 15' and adjacent photodiode pixel unit 16 as shown in FIG. 8. In this case, the fabrication method may be simplified because an additional mask process may be not required. However, it is required to form the gap G between dummy photodiode layer 15' and adjacent photodiode pixel unit 161 in order to electrically insulate dummy photodiode layer 15' from adjacent photodiode pixel unit 161. Such an embodiment will be described in more detail with FIG. 8.

Figure 4B:
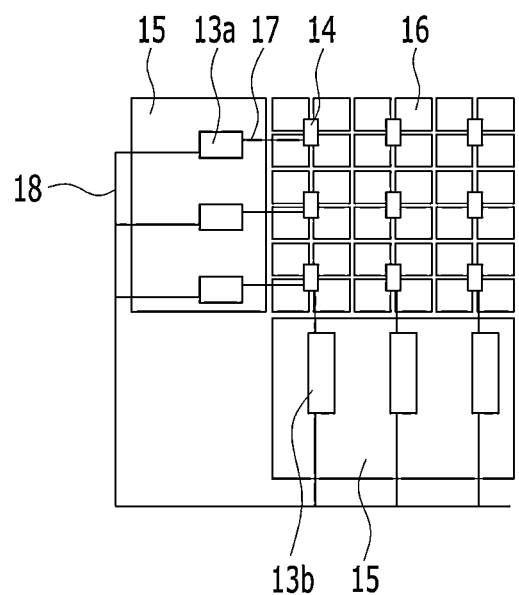
FIG. 4B is a top view illustrating an internal structure of an X-ray detector in accordance with at least one embodiment.

FIG. 4B is a top view illustrating an internal structure of an X-ray detector in accordance with at least one embodiment.

As shown in FIG. 4B, dummy layer 15 may be formed in peripheral area 12, and column and row ICs may be formed on dummy layer 15. In particular, the line printing process is performed after forming column and row ICs 13 on dummy layer 15 and forming pixel ICs 14 on photodiode 16. That is, data lines 17a and 17b are formed to couple column and row ICs 13 formed on dummy layer 15 and pixel IC 14 formed on photodiode layer 16. Further, column and row ICs 13a and 13b are coupled to a power supply (not shown) through power lines 18 by the line printing process. Since there is no height difference Hd due to dummy layer 15, it is possible to minimize line defects caused during the line printing process.

Figure 5:
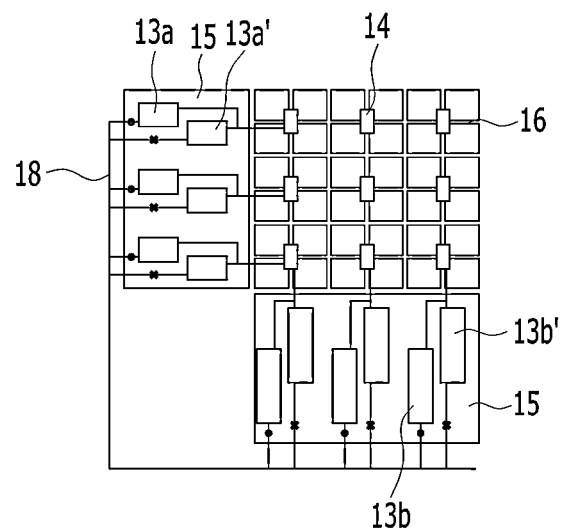
FIG. 5 is a top view illustrating an internal structure of an X-ray detector in accordance with another embodiment.

FIG. 5 is a top view of an X-ray detector in accordance with another embodiment. Referring to FIG. 5, the X-ray detector according to another embodiment may have secondary column and row ICs 13a' and 13b' for improving fabrication fault tolerance. That is, after forming primary column and row ICs 13a and 13b, secondary column and row ICs 13a' and 13b' may be formed corresponding to primary column and row ICs 13a and 13b.

In particular, such secondary column and row ICs 13a' and 13b' may be printed on dummy layer 15 using the same micro transfer printing technology. Secondary column and row ICs 13a' and 13b' which may be activated when a primary column and row micro integrated chips are malfunctioning. Such a secondary column and row ICs are formed for improving fabrication fault tolerance.

Figure 6:
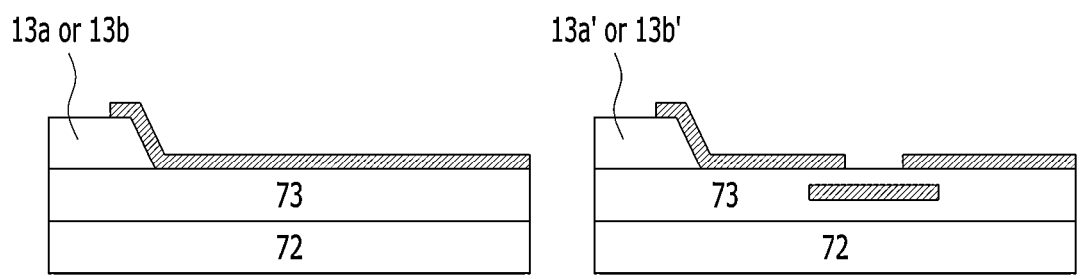
FIG. 6 is a diagram for describing deactivating primary column and row IC and activating secondary column and row IC in accordance with one embodiment.
Figure 6:
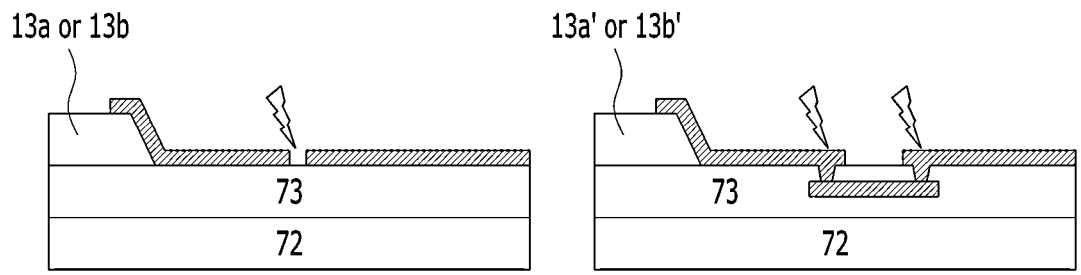

FIG. 6 is a diagram for describing deactivating primary column and row IC and activating secondary column and row IC in accordance with one embodiment. Referring to FIG. 6, an inspection process may be performed after fabricating the X-ray detector. If primary column and row ICs 13a and 13b does not pass (e.g., failed) the inspection process, primary column and row ICs 13a and 13b may be deactivated by performing laser cutting. That is, a metal line connected to primary column and row ICs 13a and 13b may be cut using a laser. Further, secondary column and row ICs 13a' and 13b' may be activated by performing laser weaving. That is, a metal line may be connected to secondary column and row ICs 13a' and 13b' by laser weaving as shown in FIG. 6.

Figure 7:
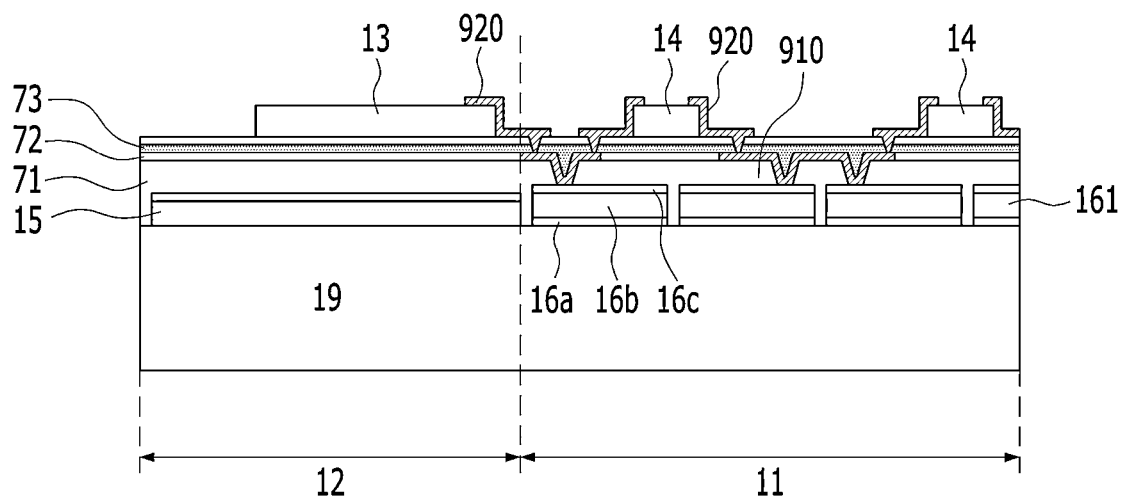
FIG. 7 is a cross-sectional view of a predetermined section in a peripheral area and a pixel area of an X-ray detector in accordance with one embodiment.

As shown, due to secondary column and row ICs 13a' and 13b' it is possible to improve fabrication fault tolerance in accordance with an embodiment. Hereinafter, a structure of an X-ray detector according to embodiments will be described in more detail with FIG. 7 and FIG. 8. FIG. 7 is a cross-sectional view of a predetermined section in a peripheral area and a pixel area of an X-ray detector in accordance with one embodiment.

Referring to FIG. 7, X-ray detector 10 may be divided into peripheral area 12 and pixel area 11 in accordance with at least one embodiment. X-ray detector 10 may include photodiode layer 16 formed on base substrate 19 within pixel area 11. Photodiode layer 16 may include first electrode 16a, photodiode 16b, and second electrode 16c. First electrode 16a may be referred to as a bottom electrode or a common electrode. Further, second electrode 16c may be referred to as a top electrode. First electrode 16a may be formed on base substrate 19.

In accordance with one embodiment, X-ray detector 10 may include dummy layer 15 formed on base substrate 19 within peripheral area 12. As shown in FIG. 7, dummy layer 15 may be formed at the same level of photodiode layer 16 in pixel area 11.

Figure 11:
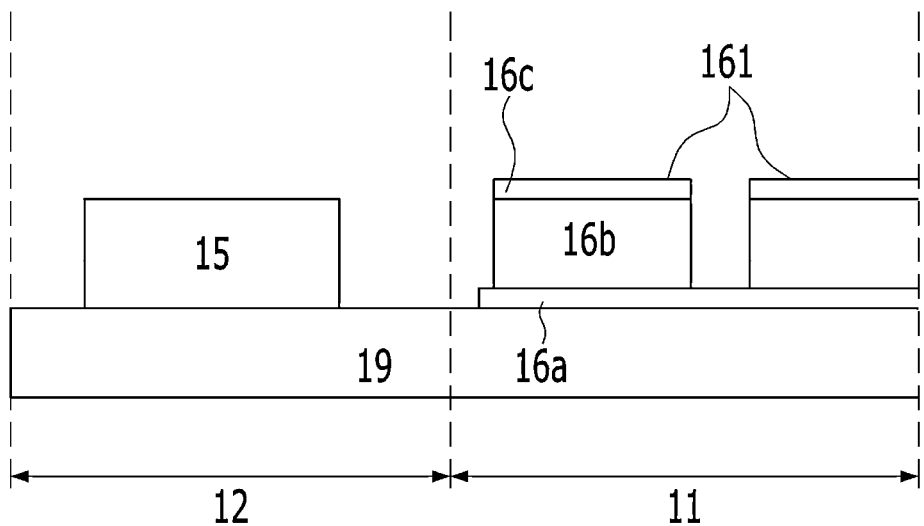

Dummy layer 15 may be formed on base substrate 19 within peripheral area 12 and patterned according to predetermined factors of column and row micro integrated chip (IC) printed thereon. For example, the predetermined factors may be a size and a shape of column and row IC 74. FIG. 11 shows dummy layer 15 formed and patterned on base substrate 19. In accordance with at least one embodiment, dummy layer 15 may be formed to have height similar or equal to that of photodiode layer 16. However, the embodiments are not limited thereto. The height of dummy layer 15 may be determined based on predetermined factors including types of material used for forming an interlayer dielectric layer and an adhesive layer and a tolerable range of lines to be printed to couple column and row ICs and pixel ICs.

In accordance with at least one embodiment, dummy layer 15 may be formed with interlayer dielectric material such as $SiO_2$ or $SiN_x$. In accordance with another embodiment, epoxy resin may be used for forming dummy layer 15. In accordance with at least one embodiment, dummy layer 15 may be formed using various fabricating method. For example, in case of a-Si photodiode, a large surface vapor deposition method may be used. The large surface vaper deposition method may include plasma-enhanced chemical vapor deposition (PECVD) and chemical vapor deposition (CVD).

In case of interlayer dielectric material (e.g., $SiO_2$, $SiN_x$), a large surface vapor deposition method may be used for forming dummy layer 15, such as PECVD, CVD, and physical vapor deposition (PVD).

In case of polymer/epoxy resin, dummy layer may be formed by i) performing spray-coating or slot-die coating to apply (e.g., depositing) polymer/epoxy resin on base substrate 19, ii) performing one of ultraviolet (UV)-hardening, thermo-hardening, and natural hardening for hardening the applied polymer/epoxy resin, and iii) patterning the hardened polymer/epoxy resin.

In accordance with at least one embodiment, photodiode layer 16 and dummy layer 15 may be manufactured using a TFT process.

X-ray detector 10 may include first interlayer dielectric layer 71 formed on photodiode layer 16 and first metal line 910 formed on first interlayer dielectric layer 71 to be contacted to top electrode 16c of photodiode 16b.

X-ray detector 10 may include second interlayer dielectric layer 72 formed on first metal line 75 and adhesive layer 73 formed on second interlayer dielectric layer 72.

X-ray detector 10 may include pixel ICs 14 each controlling at least two of photodiode pixel units 161 and metal contacts connecting pixel driving ICs to corresponding photodiode pixel units 161. X-ray detector 10 may further include column and row ICs 13 and metal lines 920 connected to corresponding pixel ICs 14.

In accordance with at least one embodiment, a plurality of pixel ICs 14 and column and row ICs 13 may be manufactured separately from the photodiode layer 16 and dummy layer 15 and printed on photodiode layer 16 and dummy layer 15 using the micro-transfer printing technology after forming contact holes in photodiode layer 16.

Then, metal lines 920 may be printed or formed to connect column and row ICs 13 to pixel ICs 14. As described, the plurality of pixel ICs 14 and column and row ICs 13 may be manufactured using a CMOS process and printed on photodiode layer 16 and dummy layer 15 using the micro-transfer technology. Accordingly, column and row ICs 13 and pixel ICs 14 may be manufactured with high precision (e.g., nanometer level) to have a high image quality.

In accordance with another embodiment, X-ray detector 10 may further include secondary column and row ICs 13a' and 13b' as shown in FIG. 5. Such secondary column and row ICs 13a' and 13b' may be formed through the same micro-transfer printing method used for forming primary column and row ICs 13. After forming secondary column and row ICs 13a and 13b, an additional line printing process may be performed for connecting or pre-connecting secondary column and row ICs 13a and 13b to pixel ICs 14.

FIG. 8 shows an X-ray detector in accordance with another embodiment. Referring to FIG. 8, X-ray detector 10 may have a structure similar to that shown in FIG. 7 except i) dummy photodiode layer 15' formed on base substrate 19 and ii) gap G formed between dummy photodiode layer 15' and adjacent photodiode pixel unit 161.

In accordance with another embodiment, X-ray detector 10 may include dummy photodiode layer 15' formed on base substrate 19 in peripheral area 12. Such dummy photodiode layer 15' may be formed by continuously forming photodiode layer 16 on base substrate 19 from pixel area 11 to peripheral area 12 and patterning photodiode layer 16 in pheripheral area 12 to dummy photodiode layer 15' and photodiode layer 16 in pixel area 11 to a plurality of photodiode pixel units 161.

In accordance with another embodiment, X-ray detector 10 may further have gap G between dummy photodiode layer 15' and adjacent photodiode pixel unit 161. The gap G between dummy photodiode layer 15' and adjacent photodiode pixel unit 161 electrically insulates dummy photodiode layer 15' from adjacent photodiode pixel unit 161.

X-ray detector 10 shown in FIG. 8 may have a structure to be manufactured through simplified fabrication process because an additional mask process may be not required.

The other constituent elements of X-ray detector 10 may be already described in detail with reference to FIG. 7. Accordingly, the detailed description of fabricating the same constituent elements will be omitted herein.

Hereinafter, a method of fabricating an X-ray detector according to the embodiments of the present disclosure will be described with reference to FIG. 9 to FIG. 20.

Figure 9:
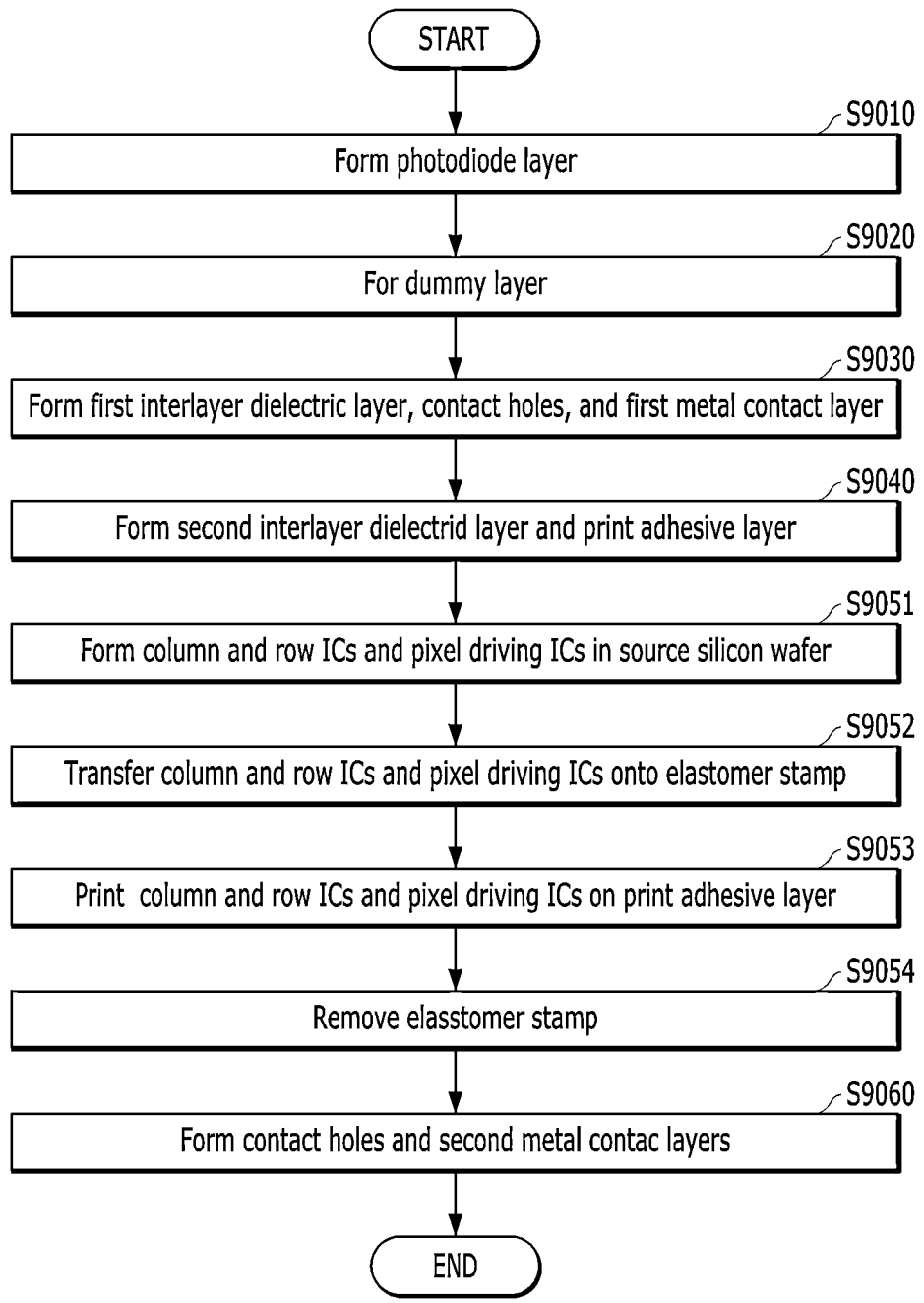
FIG. 9 is a flowchart illustrating a method of fabricating an X-ray detector having a fabrication fault tolerant structure according to at least one embodiment of the present disclosure.

FIG. 9 is a flowchart illustrating a method of fabricating an X-ray detector having a fabrication fault tolerant structure according to at least one embodiment of the present disclosure. FIG. 10 to FIG. 16 are cross-sectional views for describing a corresponding fabrication process in manufacturing the X-ray detector in accordance with at least one embodiment.

Figure 10:
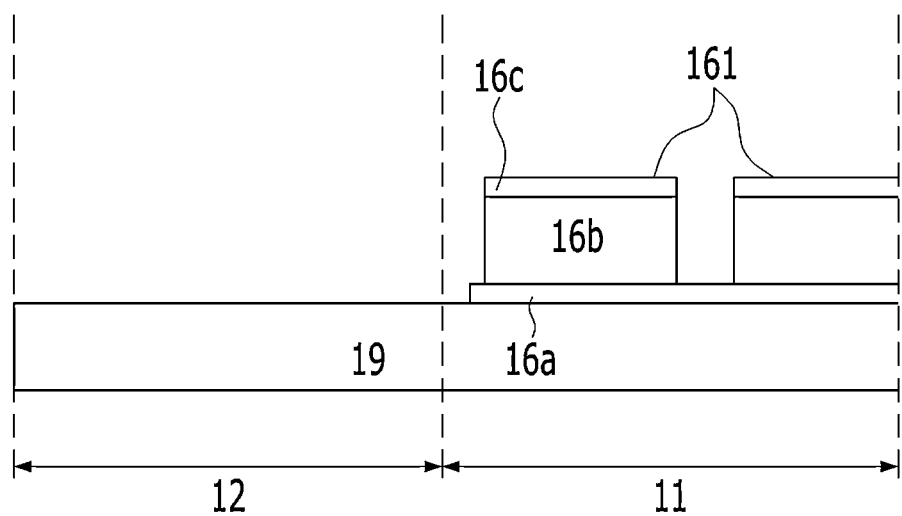
FIG. 10 to FIG. 16 are cross-sectional views for describing a corresponding fabrication process in manufacturing the X-ray detector in accordance with at least one embodiment.

Referring to FIG. 9, photodiode layer 16 may be formed within pixel area 11 at step S9010. That is, photodiode layer 16 may be formed on base substrate 19 in pixel area 11 and patterned to a plurality of photodiode pixel units 161 at step S9010. For example, photodiode layer 16 may be formed as an amorphous silicon PIN layer structure and have a thickness of about 0.8 um to about 1.2 um. FIG. 10 illustrates photodiode layer 16 formed on base substrate 19 and patterned to a plurality of photodiode pixel units 161.

In particular, photodiode layer 16 may be formed by i) forming a common bottom electrode layer (e.g., first electrode 16a) on base substrate 19, ii) forming a photodiode layer on the common bottom electrode layer, iii) a forming top electrode layer on the photodiode layer, and iv) patterning the resultant to a plurality of pixel photodiode units 161. As a result, each pixel photodiode units 161 may include first electrode 16a (e.g., common bottom electrode), photodiode 16b formed on first electrode 16a, and second electrode 16c formed on photodiode 16b, as shown in FIG. 10. Base substrate 19 may be made of material having flexible property. First electrode 16a may be made of indium tin oxide (ITO) or indium zinc oxide (IZO). First electrode 16a may be an ITO glass substrate or an IZO glass substrate, but the embodiments of the present disclosure are not limited thereto. In particular, first electrode 16a may be a transparent layer for a back side illumination type X-ray detector. However, first electrode 16a may be not a transparent layer for a front side illumination type X-ray detector. Photodiode 16b may be made of amorphous silicon (a-Si) or organic silicon. Photodiode 16b may be formed by forming a i-Si layer on common bottom electrode 16a, forming a p-Si layer on the i-Si layer, and forming an n-Si layer on the p-Si layer.

Second electrode 16c may be made of indium tin oxide (ITO) or indium zinc oxide (IZO). Second electrode 16c may be an ITO glass substrate or an IZO glass substrate, but the embodiments of the present disclosure are not limited thereto. In particular, second electrode 16c may be a transparent layer for a front side illumination type X-ray detector. However, second electrode 16c may be not a transparent layer for a back side illumination type X-ray detector. As described, such photodiode layer 16 may be formed using the TFT process in accordance with at least one embodiment. Photodiode layer 16 may be formed as a continuous layer, thereby minimizing a unit manufacturing price. Furthermore, photodiode layer 16 may be formed in an Island array structure through patterning. That is, as shown, a plurality of photodiode pixel units 161 is formed thereon in a form of matrix. In this case, the crosstalk between adjacent photodiodes may be minimized.

At step S9020, dummy layer 15 may be formed on base substrate 19 within peripheral area 12 and patterned according to predetermined factors of column and row micro integrated chip (IC) printed thereon. For example, the predetermined factors may be a size and a shape of column and row IC 74. FIG. 11 shows dummy layer 15 formed and patterned on base substrate 19.

In accordance with at least one embodiment, dummy layer 15 may be formed with interlayer dielectric material such as $SiO_2$ or $SiN_x$. In accordance with another embodiment, epoxy resin may be used for forming dummy layer 15.

In accordance with at least one embodiment, dummy layer 15 may be formed using various fabricating method. For example, in case of a-Si photodiode, a large surface vapor deposition method may be used. The large surface vaper deposition method may include plasma-enhanced chemical vapor deposition (PECVD) and chemical vapor deposition (CVD).

In case of interlayer dielectric material (e.g., $SiO_2$, $SiN_x$), a large surface vapor deposition method may be used for forming dummy layer 15, such as PECVD, CVD, and physical vapor deposition (PVD).

In case of polymer/epoxy resin, dummy layer may be formed by i) performing spray-coating or slot-die coating to apply polymer/epoxy resin on base substrate 19, ii) performing one of ultraviolet (UV)-hardening, thermo-hardening, and natural hardening for hardening the applied polymer/epoxy resin, and iii) patterning the hardened polymer/epoxy resin.

Dummy layer 15 may be formed in the peripheral area to compensate the height difference Hd between column and row ICs 13 and pixel ICs 14 in accordance with one embodiment. Dummy layer 15 may be formed to have height similar or equal to that of photodiode layer 16. However, the embodiments are not limited thereto. The height of dummy layer 15 may be determined based on predetermined factors including types of material used for forming an interlayer dielectri layer and an adhesive layer and a tolerable range of lines to be printed to couple column and row ICs and pixel ICs. Accordingly, forming dummy layer may minimize line defect in the post line printing process.

Figure 12:
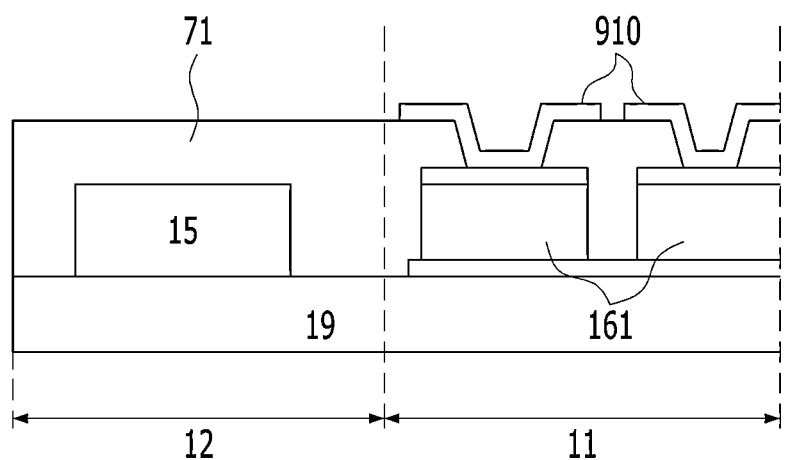

At step S9030, first interlayer dielectric (ILD) layer 71 may be formed on dummy layer 15 and a plurality of photodiode pixel units 161, contact holes may be formed on each photodiode, and metal contact layer 910 may be formed in accordance with at least one embodiment. For example, first inter layer dielectric layer 71 may be formed on dummy layer 15 and a plurality of photodiode pixel units 161 to cover all photodiodes and gaps between adjacent photodiode pixel units. First interlayer dielectric layer may be formed with $SiO_2$ or $SiN_x$ with a thickness of about 0.5 um to about 5 um. In case of Proto, $SiN_x$ may be used with a thickness of about 1.2 um. Further, a plurality of metal contact holes 121 may be formed in first interlayer dielectric layer 71 as shown in FIG. 12. For example, one metal contact hole may be formed on each photodiode pixel unit 161 to expose second electrode 16c.

Further, first metal contact layer 910 may be formed to fill first contact hole and to extend along the top surface of first interlayer dielectric layer 71 in predetermined length, as shown in FIG. 12.

Figure 13:
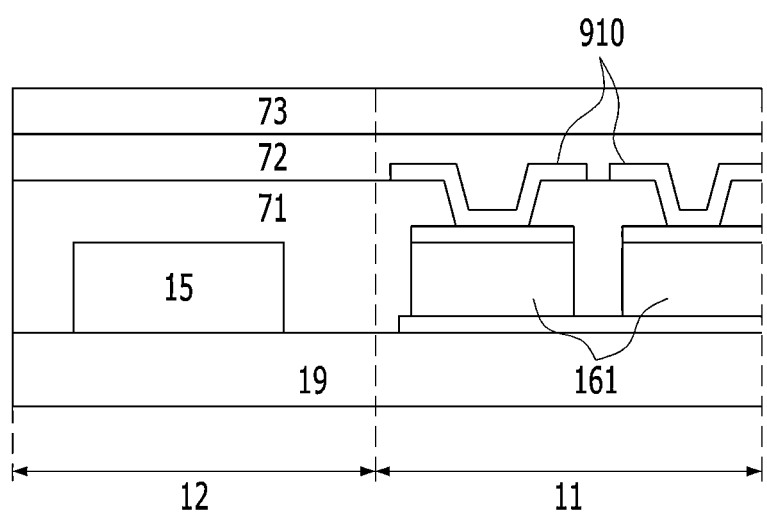

At step S9040, second interlayer dielectric layer 72 may be formed on metal contact layer 910 and first ILD layer 71, and print adhesive layer 1110 may be formed on second interlayer dielectric (ILD) layer 72, as shown in FIG. 13. Second interlayer dielectric layer 72 may be formed with $SiO_2$ or $SiN_x$ with a thickness of about 0.5 um to about 10 um. In case of Proto, $SiO_2$ may be used with a thickness about 4.0 um. Print adhesive layer 1110 may be made of resin and a thickness of about 0.5 um. To about 5 um.

Print adhesive layer 1110 may be formed for printing column and row integrated chips (ICs) 13 and pixel driving integrated chips (ICs) 14 thereon. That is, print adhesive layer 1110 formed on dummy layer 15 and photodiode layer 16 may be a target panel.

At step S9050, column and row integrated chips 13 and pixel driving integrated chips (ICs) 14 may be printed on print adhesive layer 1100. Each column and row integrated chip may be positioned to be aligned with a pixel array, and each pixel driving IC may be positioned between two adjacent pixels, as shown in FIG. 2 or FIG. 4B.

Hereinafter, a micro transfer printing process will be described with reference to FIG. 4A, FIG. 4B, and FIG. 15. In particular, FIG. 15 shows a micro transfer printing process for printing a plurality of column and row integrated chips and pixel driving micro integrated chips on a dummy layer and a photodiode layer in accordance with at least one embodiment.

Figure 15:
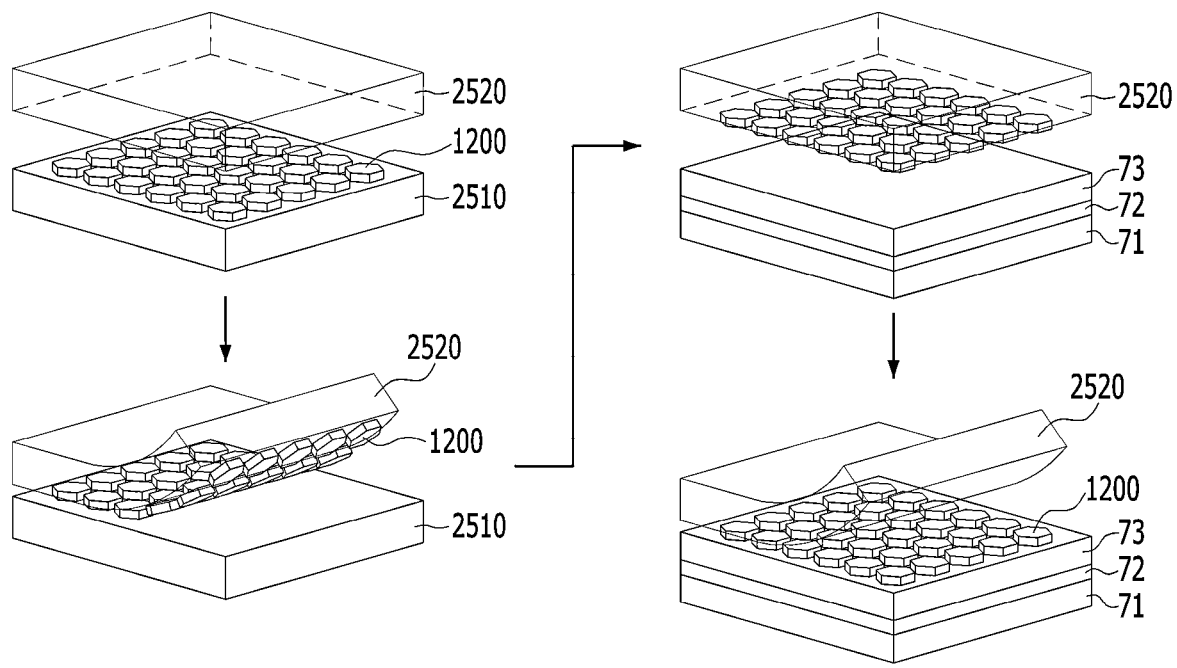

Referring to FIG. 4A, FIG. 4B, and FIG. 15, at step S9051, column and row integrated chips 13 and pixel driving integrated chips (ICs) 14 may be fabricated in source silicon wafer 2510. A CMOS process may be performed in order to fabricate an IC with high precision (e.g., micrometer level) to provide a high image quality. Then, at step S9052, column and row integrated chips 13 and pixel driving integrated chips (ICs) 14 on source silicon wafer 2510 may be transferred onto elastomer stamp 2520. At step S9053, column and row integrated chips 13 and pixel driving integrated chips 14 may be printed on print adhesive layer 73 above dummy layer 15 and photodiode layer 16 by pressing elastomer stamp 2520 on target panel 2530 (e.g., print adhesive layer 73 on dummy layer 15 and photodiode layer 16) with predetermined conditions. At step S9054, elastomer stamp 2520 may be removed after printing.

Column and row integrated chips 13 may be printed on print adhesive layer 1110 after printing pixel driving integrated chips 14 first. That is, two separated processes may be performed with two separated stamps in accordance with another embodiment.

Figure 16:
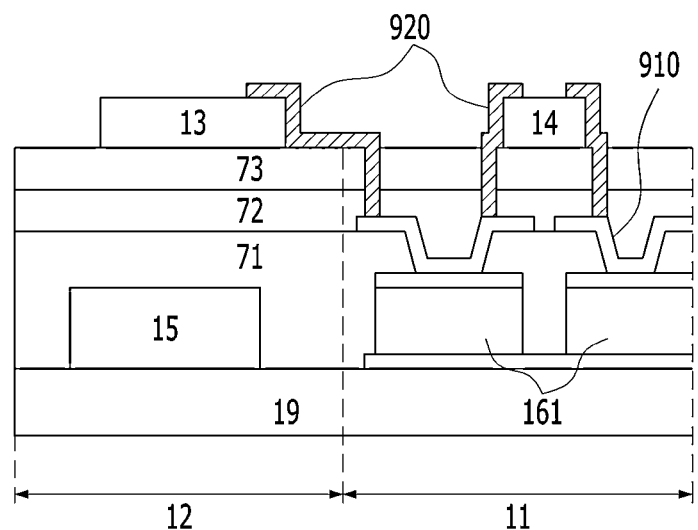

At step S9060, contact holes may be formed at one side of column and row integrated chip 13 and both sides of each pixel driving IC 14 to expose first metal contact layer 910 through second ILD layer 72 and print adhesive layer 73, as shown in FIG. 16.

Figure 14:
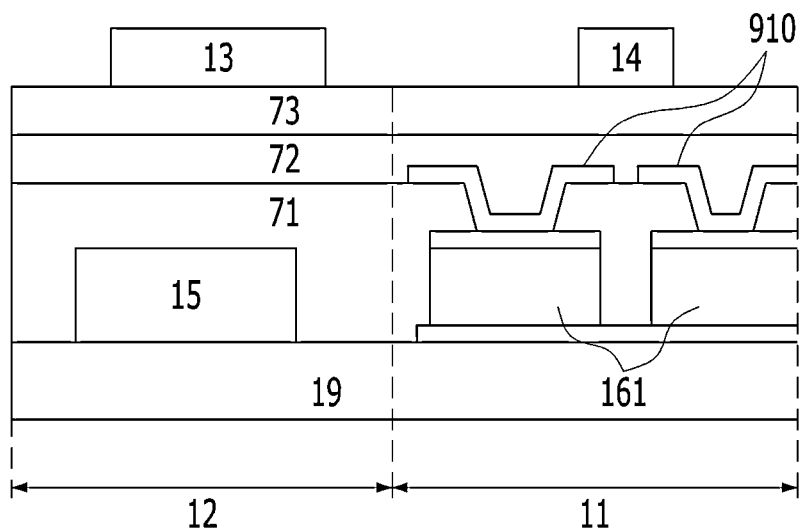

Further, second metal contact layer 920 may be formed to fill contact holes and connect column and row integrated chips 13 and both ends of pixel driving IC 14 in accordance with at least one embodiment, as shown in FIG. 14. Accordingly, column and row integrated chips 13 and each end of pixel driving IC 13 may be connected to each other and to corresponding photodiode 16.

In accordance with another embodiment of the present disclosure, column and row ICs 13 and pixel driving IC 14 may be formed directly on first ILD layer 71 and connected to corresponding photodiodes 16 without forming second ILD layer 72 and print adhesive layer 73 when first ILD layer 71 has moisture proofing priority and adhesive priority. In this case, a manufacturing method may be further simplified.

In accordance with still another embodiment of the present disclosure, column and row IC 13 and pixel driving IC 14 may be formed directly on second ILD layer 72 and connected to corresponding pixels 16 without forming print adhesive layer 73 when second ILD layer 72 has moisture proofing priority and adhesive priority.

As described above, dummy layer 15 may compensate the height difference between column and row IC 13 and pixel driving IC 14, which is caused when column and row IC 13 is printed directly on base substrate 19 without forming dummy layer 15 as shown in FIG. 3A. Accordingly, X-ray detector 10 according to an embodiment may have a structure that minimizes line defects that may be caused when column and row ICs are coupled to pixel driving ICs through the line printing process.

As described, an additional layer different from a photodiode layer may be formed within peripheral area 12 as a dummy layer for compensating the height difference in accordance with one embodiment. Such a structure might require an additional process step for forming the additional layer formed on base substrate 19. However, in accordance with another embodiment, a photodiode layer may be continuously formed in peripheral area 12 to be extended from the photodiode layer formed in pixel area 11 as a dummy layer to compensate the height difference. In this case, the additional forming process may be not required. Hereinafter, a method of fabricating such a structure of X-ray detector 10 will be described hereinafter with reference to FIG. 17 to FIG. 20.

Figure 17:
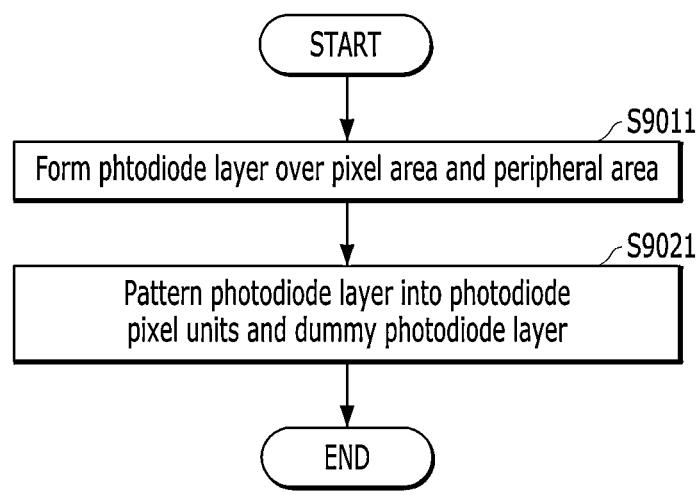
FIG. 17 is a flowchart illustrating a method of fabricating an X-ray detector having a fabrication fault tolerant structure according to another embodiment of the present disclosure.
Figure 18:
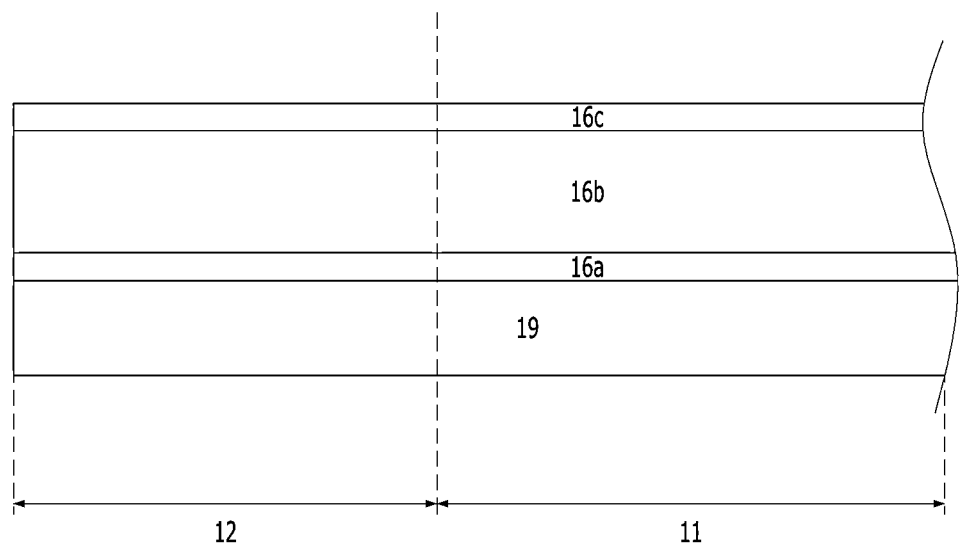
FIG. 18 to FIG. 20 are cross-sectional views for describing a corresponding fabrication process in manufacturing the X-ray detector in accordance with another embodiment.
Figure 19:
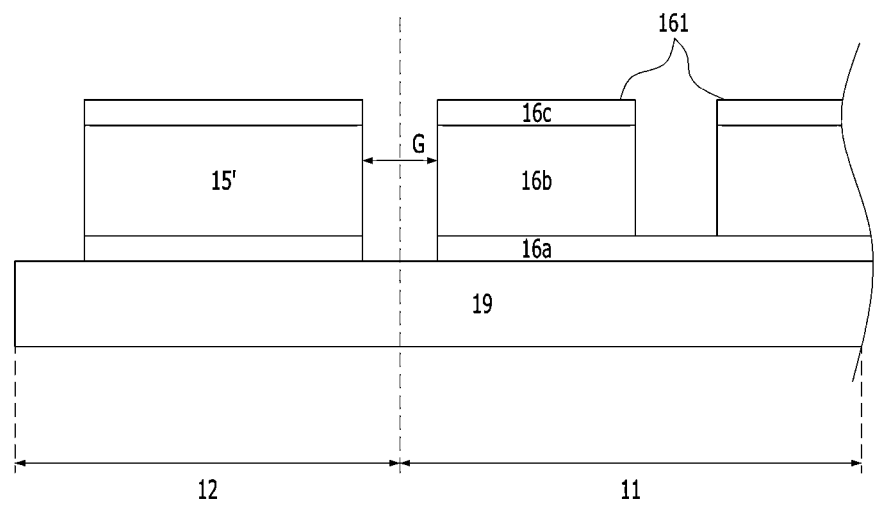
Figure 20:
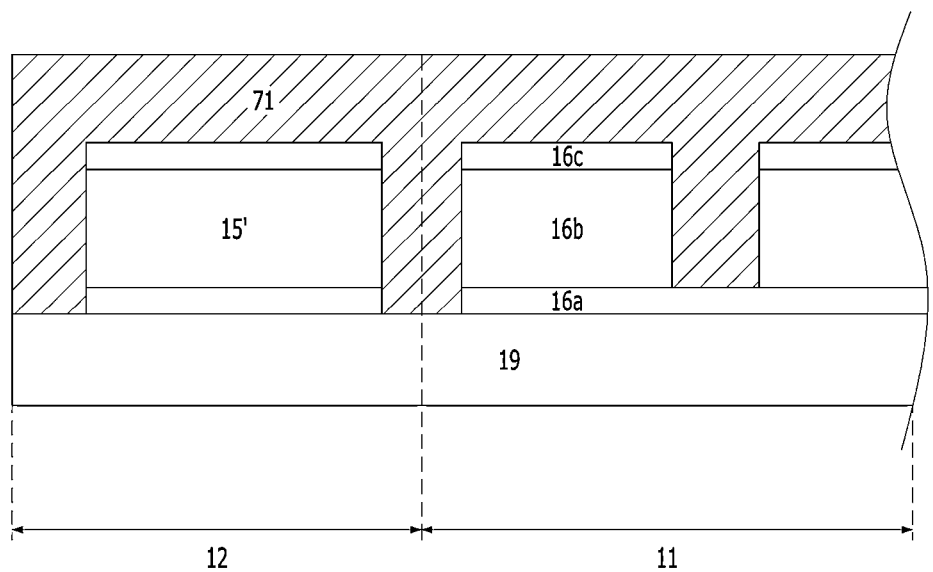

FIG. 17 is a flowchart illustrating a method of fabricating an X-ray detector having a fabrication fault tolerant structure according to another embodiment of the present disclosure. FIG. 18 to FIG. 20 are cross-sectional views for describing a corresponding fabrication process in manufacturing the X-ray detector in accordance with another embodiment.

Referring to FIG. 17, photodiode layer 16 may be formed over pixel area 11 and peripheral area 12 at step S9011. That is, photodiode layer 16 may be formed on base substrate 19 not only over pixel area 11 but also over peripheral area 12. As shown in FIG. 18, photodiode layer 16 may be formed by i) forming a common bottom electrode layer (e.g., first electrode 16a) on base substrate 19, ii) forming photodiode layer 16b on the common bottom electrode layer, and iii) a forming top electrode layer (e.g., second electrode 16c) on the photodiode layer, At step S9021, photodiode layer 16 (e.g., 16a, 16b, and 16c) may be patterned into a plurality of pixel photodiode units 161 and dummy photodiode layer 15'. Furthermore, a gap G may be formed between dummy photodiode layer 15' and adjacent pixel photodiode unit 161 for physically separating dummy photodiode layer 15' from adjacent pixel photodiode unit 161 in accordance with another embodiment.

At step S9030, first interlayer dielectric (ILD) layer 71 may be formed on dummy layer 15 and a plurality of photodiode pixel units 161, contact holes may be formed on each photodiode, and metal contact layer 910 may be formed in accordance with another embodiment. The same process steps S9040 to S9060 may be performed for completely fabricating the X-ray detector in accordance with another embodiment.

As shown, photodiode layer 16 is continuously formed over not only pixel area 11 and but also peripheral area 12 and patterned into dummy photodiode layer 16 and photodiode pixel units 161. The patterned dummy photodiode layer 16 formed on peripheral area 12 may be used a dummy layer to compensate the height difference that may cause line defects in the line printing process. Accordingly, using a part of photodiode layer 16 as the dummy layer, it is possible to minimize fabricating process steps, at least a masking process with a mask. Further, the gap G may be formed to be equal to about 5 um and not wider than about 10 nm. The gap G may insulate dummy photodiode layer 15' formed in peripheral area 12 from adjacent photodiode pixel unit 161 formed in pixel area 11.

As described, due to dummy photodiode layer 15', it is possible to minimize the line defects in accordance with one embodiment. In addition, X-ray detector 10 may further include redundant column and row ICs for improving fabrication fault tolerance in accordance with still another embodiment. Hereinafter, a method for forming secondary column and row ICs, inspecting whether one of primary and secondary column and row ICs works normally, and activating one of primary and secondary column and row ICs will be described with reference to FIG. 21 and FIG. 5 and FIG. 6.

Figure 21:
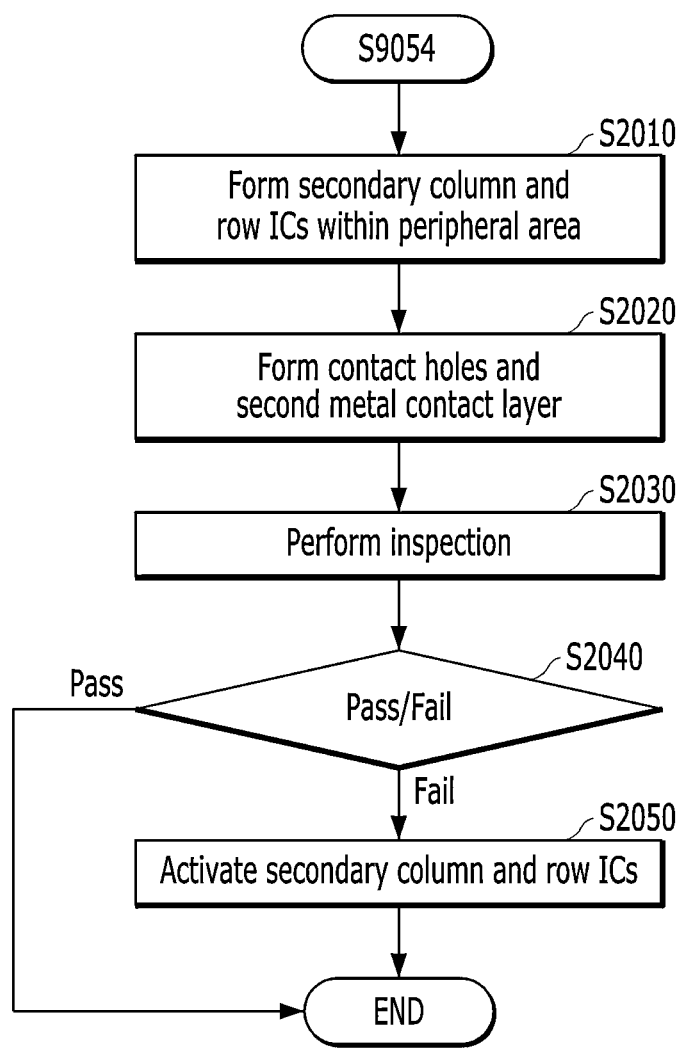
FIG. 21 is a flowchart illustrating a method for fabricating an X-ray detector having a redundant column and row IC for improving fault tolerance in accordance with still another embodiment.

FIG. 21 is a flowchart illustrating a method for fabricating an X-ray detector having a redundant column and row IC for improving fault tolerance in accordance with still another embodiment.

As shown in FIG. 19, dummy layer 15 and a plurality of photodiode pixel units 161 may be formed respectively on peripheral area 12 and pixel area 11, first and interlayer dielectric layers 71 and 72 and adhesive layer 73 may be sequentially formed on dummy layer 15 and photodiode pixel units 161 at steps S9010 to S9054.

Referring back to FIG. 21, secondary column and row ICs 13' may be formed adjacent to primary column and row ICs 13 within peripheral area 12 at step S2010. Such a process may be similar to printing primary column and row ICs 13 described in steps S9051 to S9054 of FIG. 19.

At step S2020, contact holes may be formed at one side of primary and secondary column and row integrated chips 13 and 13' and both sides of each pixel driving IC 14 to expose first metal contact layer 910 through second ILD layer 72 and print adhesive layer 73, as shown in FIG. 16.

Further, second metal contact layer 920 may be formed to fill contact holes and connect primary and secondary column and row integrated chips 13 and 13' and both ends of pixel driving IC 14 in accordance with at least one embodiment, as shown in FIG. 14 and FIG. 5. Accordingly, primary and secondary column and row integrated chips 13 and 13' and each end of pixel driving IC 13 may be connected to each other and to corresponding photodiode 16.

At step S2030, inspection may be performed to determine whether the primary column and row ICs are functioned correctly. If the inspection fails (fail-S2040), secondary column and row ICs may be activated by laser weaving and primary column and row ICs may be deactivated by laser cutting at step S2050.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, the terms "system," "component," "module," "interface,", "model" or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

The present invention can be embodied in the form of methods and apparatuses for practicing those methods. The present invention can also be embodied in the form of program code embodied in tangible media, non-transitory media, such as magnetic recording media, optical recording media, solid state memory, floppy diskettes, CD-ROMs, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium or carrier, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits. The present invention can also be embodied in the form of a bitstream or other sequence of signal values electrically or optically transmitted through a medium, stored magnetic-field variations in a magnetic recording medium, etc., generated using a method and/or an apparatus of the present invention.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

As used herein in reference to an element and a standard, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

No claim element herein is to be construed under the provisions of 35 U.S.C. § 112, sixth paragraph, unless the element is expressly recited using the phrase "means for" or "step for."

Although embodiments of the present invention have been described herein, it should be understood that the foregoing embodiments and advantages are merely examples and are not to be construed as limiting the present invention or the scope of the claims. Numerous other modifications and embodiments can be devised by those skilled in the art that will fall within the spirit and scope of the principles of this disclosure, and the present teaching can also be readily applied to other types of apparatuses. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An X-ray detector comprising:
   a photodiode layer formed on a base substrate within a pixel area and comprises a plurality of photodiode pixel units;
   a dummy layer formed on the base substrate within a peripheral area and insulated from the plurality of photodiode pixel units;
   a plurality of pixel driving integrated chips mounted on the photodiode layer;
   a plurality of primary column and row integrated chips printed on the dummy layer; and
   metal lines mounted on the pixel driving integrated chips and primary column and row integrated chips for coupling the column and row integrated chips with pixel driving integrated chips and other constituent elements,
   wherein the plurality of pixel driving integrated chips and primary column and row integrated chips are manufactured separately from the photodiode layer and the dummy layer and attached on the photodiode layer and the dummy layer, respectively.

2. The X-ray detector of claim 1, wherein the dummy layer is formed to have height similar or equal to that of the photodiode layer.

3. The X-ray detector of claim 1, wherein the dummy layer has height about 0.8 um to about 1.2 um.

4. The X-ray detector of claim 1, wherein the dummy layer is formed with interlayer dielectric material including $SiO_2$ and $SiN_x$.

5. The X-ray detector of claim 1, wherein the dummy layer is formed with epoxy resin.

6. The X-ray detector of claim 1, wherein the dummy layer is formed with the photodiode layer by continuously forming the photodiode layer in the peripheral area and patterning the photodiode layer formed in the peripheral area into the dummy layer.

7. The X-ray detector of claim 5, further comprising: a gap between the dummy layer and an adjacent photodiode pixel unit for insulating the dummy layer from the adjacent photodiode pixel unit.

8. The X-ray detector of claim 1, further comprising: a plurality of secondary column and row integrated chips formed respectively to primary column and row integrated chips within the peripheral area.

9. The X-ray detector of claim 8, wherein at least one of the secondary column and row integrated chips is activated when a corresponding primary column and row integrated chip fails to pass inspection.

10. The X-ray detector of claim 9, the secondary column and row integrated chip is activated by laser waving, and the corresponding primary column and row integrated chip is deactivated by laser cutting.

11. A method for fabricating an X-ray detector having a fabrication fault tolerant structure, the comprising:
    forming a photodiode layer on a base substrate within a pixel area, patterning the photodiode layer into a plurality of photodiode pixel units;
    forming and patterning a dummy layer on the base substrate within a peripheral area;
    printing a plurality of pixel driving integrated chips on the photodiode layer;
    printing a plurality of primary column and row integrated chips on the dummy layer; and
    printing metal lines on the pixel driving integrated chips and primary column and row integrated chips to couple the column and row integrated chips with pixel driving integrated chips and other constituent elements,
    wherein the plurality of pixel driving integrated chips and primary column and row integrated chips are fabricated separately from the photodiode layer and the dummy layer and attached on the photodiode layer and the dummy layer, respectively.

12. The method of claim 11, wherein the forming and patterning a dummy layer comprise forming the dummy layer to have height similar or equal to that of the photodiode layer.

13. The method of claim 11, wherein the dummy layer formed to have height about 0.8 um to about 1.2 um.

14. The method of claim 11, wherein the dummy layer is formed with interlayer dielectric material including SiO2 and SiNx.

15. The method of claim 11, wherein the dummy layer is formed with epoxy resin.

16. The method of claim 11, wherein the forming and patterning a dummy layer comprises:
    continuously forming the photodiode layer from the pixel area to the peripheral area; and
    patterning the photodiode layer formed in the peripheral area to the dummy layer.

17. The method of claim 15, further comprising: forming a gap between the dummy layer and an adjacent photodiode pixel unit for insulating the dummy layer from the adjacent photodiode pixel unit.

18. The method of claim 11, further comprising: printing a plurality of secondary column and row integrated chips respectively to primary column and row integrated chips within the peripheral area.

19. The method of claim 18, wherein at least one of the secondary column and row integrated chips is activated when a corresponding primary column and row integrated chip fails to pass inspection.

20. The method of claim 19, the secondary column and row integrated chip is activated by laser waving, and the corresponding primary column and row integrated chip is deactivated by laser cutting.

* * * * *